(12) United States Patent
Ni et al.

(10) Patent No.: US 10,508,073 B2
(45) Date of Patent: Dec. 17, 2019

(54) METHOD FOR PREPARING ACETAL CARBONYL COMPOUND

(71) Applicant: Dalian Institute of Chemical Physics, Chinese Academy of Sciences, Shahekou Dalian (CN)

(72) Inventors: Youming Ni, Shahekou Dalian (CN); Wenliang Zhu, Shahekou Dalian (CN); Yong Liu, Shahekou Dalian (CN); Hongchao Liu, Shahekou Dalian (CN); Zhongmin Liu, Shahekou Dalian (CN); Miao Yang, Shahekou Dalian (CN); Peng Tian, Shahekou Dalian (CN)

(73) Assignee: Dalian Institute of Chemical Physics, Chinese Academy of Sciences, Shahekou Dalian (CN)

( * ) Notice: Subject to any disclaimer, the term of this patent is extended or adjusted under 35 U.S.C. 154(b) by 31 days.

(21) Appl. No.: 15/743,698

(22) PCT Filed: Dec. 8, 2015

(86) PCT No.: PCT/CN2015/096647
§ 371 (c)(1),
(2) Date: Jan. 11, 2018

(87) PCT Pub. No.: WO2017/012245
PCT Pub. Date: Jan. 26, 2017

(65) Prior Publication Data
US 2018/0201567 A1    Jul. 19, 2018

(30) Foreign Application Priority Data
Jul. 20, 2015  (CN) .......................... 2015 1 0426676

(51) Int. Cl.
C07C 67/37       (2006.01)
C07C 69/708      (2006.01)
B01J 29/85       (2006.01)
B01J 35/04       (2006.01)

(52) U.S. Cl.
CPC .............. *C07C 67/37* (2013.01); *B01J 29/85* (2013.01); *B01J 35/04* (2013.01); *C07C 69/708* (2013.01); *B01J 2229/183* (2013.01); *B01J 2523/17* (2013.01); *B01J 2523/18* (2013.01); *B01J 2523/32* (2013.01); *B01J 2523/824* (2013.01); *B01J 2523/828* (2013.01); *B01J 2523/842* (2013.01); *B01J 2523/845* (2013.01); *B01J 2523/847* (2013.01); *C07C 2529/85* (2013.01)

(58) Field of Classification Search
CPC ........ C07C 67/37; C07C 69/708; B01J 29/85; B01J 35/04
See application file for complete search history.

(56) References Cited

U.S. PATENT DOCUMENTS

| 4,792,620 A | * | 12/1988 | Paulik | ................. B01J 31/0231 |
| | | | | 560/232 |
| 2010/0105947 A1 | * | 4/2010 | Celik | ...................... C07C 67/37 |
| | | | | 560/232 |
| 2015/0202603 A1 | * | 7/2015 | Schmidt | .................. B01J 29/70 |
| | | | | 585/640 |

FOREIGN PATENT DOCUMENTS

| CN | 1525940 A | 9/2004 | |
| CN | 103172516 A | 6/2013 | |
| CN | 103172517 A | 6/2013 | |
| CN | 103831124 A | 6/2014 | |
| CN | 104119228 A | 10/2014 | |
| CN | 104725224 A | 6/2015 | |
| EP | 0088529 A2 | 9/1983 | |
| EP | 3088381 A1 | 11/2016 | |
| WO | WO-2008073096 A1 * | 6/2008 | ............. C07C 51/09 |
| WO | 2015096009 A1 | 7/2015 | |

OTHER PUBLICATIONS

Norskov et al, Nature Chemistry, Towards the Computational Design of Solid Catalysts, 2009, 1, pp. 37-46. (Year: 2009).*
Hacking, Michiel, "Supplementary European Search Report, European Application No. EP 15 89 8801", Jul. 18, 2018, European Patent Office.
Wang, Ying, "International Search Report, International Application No. PCT/CN2015/096647", Apr. 28, 2016, World Intellectual Property Office.
Zhang, Baoji, "Search Report, Chinese Application No. 2015104266761", Apr. 9, 2018, State Intellectual Property Office.

* cited by examiner

*Primary Examiner* — Paul A Zucker
(74) *Attorney, Agent, or Firm* — Edwin A. Sisson, Attorney at Law, LLC; Jeffrey J. Banyas

(57) ABSTRACT

The present application provides a method for preparing acetal carbonyl compound used as an intermediate for producing ethylene glycol, which comprises a step in which a raw material acetal and a raw gas carbon monoxide go through a reactor loaded with a catalyst containing an acidic microporous silicoaluminophosphate molecular sieve, for carrying out a carbonylation reaction. In the method of the present invention, the conversion rate of the raw material acetal is high, and the selectivity of acetal carbonylation is high, and the catalyst life is long, and no additional solvent is needed in the reaction process, and the reaction condition is relatively mild, and the process is continuous, showing the potential for industrial application. Moreover, the product of acetal carbonyl compound can be used for producing ethylene glycol by hydrogenation followed by hydrolysis.

14 Claims, 1 Drawing Sheet

METHOD FOR PREPARING ACETAL CARBONYL COMPOUND

PRIORITIES AND CROSS REFERENCES

This application claims priority from International Application No. PCT/CN2015/096647 filed on 8 Dec. 2015 and Chinese Application No. 201510426676.1 filed on 20 Jul. 2015, the teachings of each of which are incorporated by reference herein in their entirety.

TECHNICAL FIELD

The present application refers to a method for preparing acetal carbonyl compound which is used as an intermediate for producing ethylene glycol.

BACKGROUND

Ethylene glycol is an important chemical raw material and strategic material in China. Ethylene glycol can be used to produce polyester which can be further processed to produce terelyene, PET bottles and thin films, explosives, glyoxal. Ethylene glycol can also be used as antifreeze, plasticizers, hydraulic fluids, solvents and so on. In 2009, the Chinese import quantum of ethylene glycol was more than 5.80 million tons. It is expected that in 2015, Chinese ethylene glycol demand will reach 11.20 million tons, and Chinese production capacity of ethylene glycol will be about 5 million tons, and the supply and demand gap will be 6.20 million tons. Therefore, there is a good market prospect for development and application of new production technology of ethylene glycol in china. Internationally, ethylene oxide is mainly obtained by oxidation of ethylene generated from petroleum cracking, and ethylene glycol is mainly obtained by hydration of ethylene oxide. In view of the current state of Chinese energy source structure of being rich in coal, lack in oil and gas, and the crude oil price being kept at a high level for a long time, the process of producing ethylene glycol from coal as a new technique in coal chemistry industry is the most practical choice of the coal chemistry industry in the future, because it can ensure the national energy safety and make full use of the coal resource in China.

At present, the relatively mature technology in China is a complete set of technology containing CO gas phase catalytic synthesis oxalate ester and catalytic hydrogenation synthesis of ethylene glycol from oxalate ester, developed by Fujian Institute of Research on the Structure of Matter, Chinese Academy of Sciences.

In early December 2009, the coal-to-ethylene glycol project of GEM Chemical Company, Tongliao, Neimenggu with a yearly output of 200 thousand tons, has been successful in getting through the entire process in the first-stage project and produced a qualified ethylene glycol product, which is the world first industrial demonstration device, attracting industry attention.

However, due to relatively more industrial units, high requirement of industrial gases purity, usage of noble metal catalysts in the process of oxidative coupling, and utilization of nitrogen compounds with potential environment pollution, the technology process has been restricted in economic efficiency, environmental protection, energy-saving performance and further industrial scale-up.

Polyoxymethylene dimethyl ethers (or polymethoxy acetal) with molecular formula of $CH_3O (CH_2O) nCH_3$ with n≥2, generally is abbreviated as DMMn (or PODEn). In the process of preparing polyoxymethylene dimethyl ethers, the product distribution is not very appropriate with a high selectivity of methylal and $DMM_2$ and a low selectivity of $DMM_{3-4}$ which can be used as the additives of diesel. To obtain $DMM_{3-4}$, it is necessary to contain the repeated separation and reaction steps of the side products which are produced in the preparing process, bring a high energy consumption and a low economic efficiency. Therefore, if the side products methylal and $DMM_2$ can be directly produced into more economically valuable products, it will improve the economic efficiency of the process.

In US2010/0105947A, a method for preparing methyl methoxyacetate has been disclosed, in which methyl methoxyacetate was prepared by dimethoxymethane carbonylation, in the presence of a zeolite molecular sieve catalyst. The catalyst has been selected from FAU, ZSM-5, MOR or β-zeolite. In EP0088529A2, a method for preparing methyl methoxy acetate has been disclosed, in which methyl methoxy acetate was obtained by dimethoxymethane carbonylation, in the presence of a solid catalyst. The catalyst is selected from acidic cation exchange resins, clays, zeolites, solid acids, inorganic oxides, inorganic salts and oxides. In CN104119228A, a method for preparing methyl methoxy acetate has been disclosed, in which methylal and CO were used as raw materials to prepare methyl methoxy acetate by catalytic synthesis, and the catalyst is a molecular sieve with MWW framework structure. In CN103894228A, a method for preparing methyl methoxy acetate has been disclosed, in which methylal and CO were used as raw materials to prepare methyl methoxy acetate by catalytic synthesis, and the catalyst is a solid catalyst loaded with a strong organic sulfonic acid. The supporter of the catalyst is one or more selected from activated carbon, SBA-15 and MCM-41. In CN103172517A, a method for producing methyl methoxy acetate has been disclosed, in which the methyl methoxy acetate was produced by gas-phase carbonylation of methylal and CO, in the presence of a solid acid catalyst. In recent years, Professor Alexis T. Bell from University of California Berkeley has proposed a new route to producing ethylene glycol, containing gas-phase carbonylation of methylal for preparing methoxy acetic acid methyl ester and hydrogenated hydrolysis of methoxy acetic acid methyl ester to producing ethylene glycol. And the most important step is the gas-phase carbonylation. However, because the catalyst life is short, and the concentration of methylal in raw gas is low, and the conversion rate of methylal and the selectivity of methyl methoxy acetate are not ideal, it is far from industrialization. (Angew. Chem. Int. Ed., 2009, 48, 4813-4815; J. Catal., 2010, 270, 185-195; J. Catal., 2010, 274, 150-162; WO2010/048300 A1).

SUMMARY OF THE INVENTION

The purpose of the present invention is to provide a method for preparing acetal carbonyl compound used as an intermediate for producing ethylene glycol by carbonylation.

Therefore, the present invention provides a method for preparing acetal carbonyl compound used as an intermediate for producing ethylene glycol, which comprises a step in which a raw material acetal and a raw material carbon monoxide go through a reactor loaded with a catalyst for carrying out a carbonylation reaction; wherein the catalyst contains an acidic microporous silicoaluminophosphate molecular sieve; wherein the chemical composition of the acidic microporous silicoaluminophosphate molecular sieve is expressed as $(Si_xAl_yP_z)O_2$, and x is in a range from 0.01 to 0.60, and y is in a range from 0.2 to 0.60, and z is in a range from 0.2 to 0.60, and x+y+z=1; wherein the raw material acetal is expressed as $R_1O(CH_2O)_nR_2$, and n is selected from 1, 2, 3 or 4, and $R_1$ and $R_2$ are independently selected from $C_1$-$C_3$ alkyls.

In a preferred embodiment, the acidic microporous silicoaluminophosphate molecular sieve has an 8-membered ring pore framework.

In a preferred embodiment, the acidic microporous silicoaluminophosphate molecular sieve is one or more molecular sieves selected from the molecular sieves with framework type of CHA, RHO, LEV, ERI, AEI or AFX. More preferably, the acidic microporous silicoaluminophosphate molecular sieve is one or more molecular sieves selected from SAPO-34, DNL-6, SAPO-35, SAPO-17, SAPO-18 or SAPO-56.

In a preferred embodiment, the acidic microporous silicoaluminophosphate molecular sieve contains a metal; and the mass fraction of the metal in the acidic microporous silicoaluminophosphate molecular sieve is in a range from 0% to 10%. More preferably, the mass fraction of the metal element in the acidic microporous silicoaluminophosphate molecular sieve is in a range from 0% to 2%. Further more preferably, the metal is one or more metals selected from copper, iron, gallium, silver, nickel, cobalt, palladium or platinum.

In a preferred embodiment, the metal is located at the ion-exchange sites, in the pores and channels, on the surface and/or in the framework of the acidic microporous silicoaluminophosphate molecular sieve; and the metal is introduced by one or more methods selected from situ synthesis, impregnation or ion exchange.

In a preferred embodiment, the catalyst contains a forming agent, and the mass fraction of the forming agent in the catalyst is in a range from 10% to 60%. More preferably, the mass fraction of the forming agent in the catalyst is in a range from 10% to 30%. Preferably, the forming agent is one or more compounds selected from alumina, silicon oxide or kaolin.

In a preferred embodiment, the raw material acetal is $CH_3OCH_2OCH_3$, $C_2H_5OCH_2OC_2H_5$ or $CH_3O(CH_2O)_2CH_3$, and the acetal carbonyl compound is one or more compounds selected from $CH_3$—O—(CO)—$CH_2$—O—$CH_3$, $C_2H_5$—O—(CO)—$CH_2$—O—$C_2H_5$, $CH_3$—O—(CO)—$CH_2$—O—$CH_2$—O—$CH_3$ or $CH_3$—O—$CH_2$—(CO)—O—$CH_2$—O—$CH_3$.

In a preferred embodiment, the carbonylation reaction conditions are as follows: the reaction temperature is in a range from 60° C. to 140° C., and the reaction pressure is in a range from 1 MPa to 15 MPa, and the mass space velocity of the raw material acetal is in a range from 0.1 $h^{-1}$ to 10.0 $h^{-1}$, and the molar ratio of the raw material carbon monoxide to the raw material acetal is in a range from 2:1 to 20:1, and no solvent is added. More preferably, the carbonylation reaction conditions are as follows: the reaction temperature is in a range from 70° C. to 120° C., and the reaction pressure is in a range from 3 MPa to 10 MPa, and the mass space velocity of the raw material acetal is in a range from 0.5 $h^{-1}$ to 3 $h^{-1}$, and the molar ratio of the raw material carbon monoxide to the raw material acetal is in a range from 5:1 to 15:1, and no other solvent is added.

In a preferred embodiment, the reactor is a continuous reactor which is selected from a fixed bed reactor, a tank reactor, a moving bed reactor or a fluidized bed reactor.

The present invention can bring the advantages which at least include, but are not limited to: Compared with the prior arts, the method of the present invention uses a catalyst containing the acidic microporous silicoaluminophosphate molecular sieve catalyst, with a high conversion rate of acetal and a high selectivity of acetal carbonylation. Moreover, compared with the prior arts, in the method of the present invention, the catalyst has a longer life, and no additional solvent is needed in the reaction process, and the reaction condition is relatively mild, and the process is continuous, showing the potential for industrial application.

DETAILED DESCRIPTION OF THE EMBODIMENT

Figure 1:
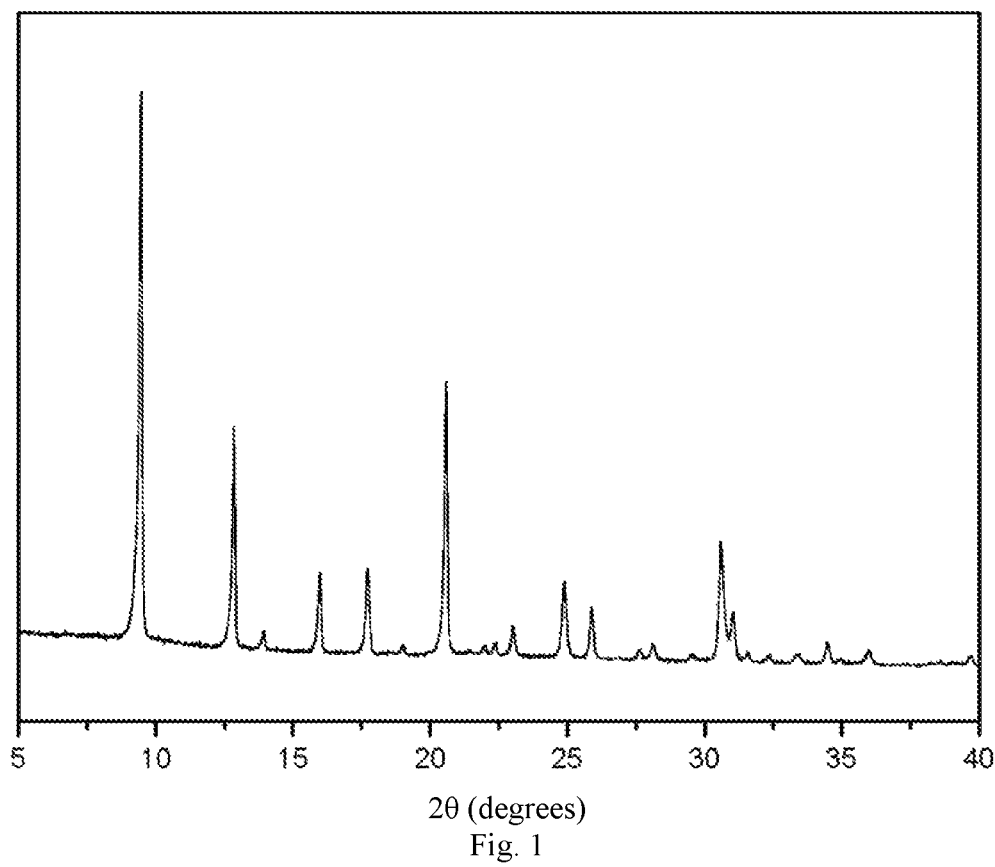
FIG. 1 is the X-ray powder diffraction (XRD) spectra of the SAPO-34 molecular sieve prepared in Example 1 of the present invention.

The present invention refers to a method for preparing acetal carbonyl compound used as an intermediate for producing ethylene glycol, which comprises a step in which a raw material acetal and a raw material carbon monoxide go through a reactor loaded with a catalyst containing an acidic microporous silicoaluminophosphate molecular sieve, for carrying out a carbonylation reaction.

Preferably, the acidic microporous silicoaluminophosphate molecular sieve is with an 8-membered ring pore framework.

Preferably, the chemical composition of the acidic microporous silicoaluminophosphate molecular sieve is expressed as $(Si_xAl_yP_z)O_2$; x, y, z respectively represents the molar number of Si, Al, P, and x is in a range from 0.01 to 0.60, and y is in a range from 0.2 to 0.60, and z is in a range from 0.2 to 0.60, and x+y+z=1.

Preferably, the acidic microporous silicoaluminophosphate molecular sieve is one or more molecular sieves selected from the molecular sieves with framework type of ABW, ACO, AEI, AEN, AFN, AFT, AFX, ANA, APC, APD, ATN, ATT, ATV, AWO, AWW, BIK, BRE, CAS, CHA, DOR, DFY, LAB, EDI, ERI, ESV, GIS, GOO, ITE, JBW, KFI, LEV, LTA, MER, MON, MTF, PAU, PHI, RHO, RTE, RTH, SAS, SAT, SAV, THO, TSC, VNI, YUG or ZON.

Preferably, the acidic microporous silicoaluminophosphate molecular sieve is one or more molecular sieves selected from the molecular sieves with framework type of CHA, RHO, LEV, ERI, AEI or AFX.

Preferably, the acidic microporous silicoaluminophosphate molecular sieve is one or more molecular sieves selected from SAPO-34, DNL-6, SAPO-35, SAPO-17, SAPO-18 or SAPO-56.

Preferably, the acidic microporous silicoaluminophosphate molecular sieve contains a metal; and the mass fraction of the metal element in the acidic microporous silicoaluminophosphate molecular sieve is in a range from 0% to 10%.

Preferably, the acidic microporous silicoaluminophosphate molecular sieve contains a metal; and the mass fraction of the metal element in the acidic microporous silicoaluminophosphate molecular sieve is in a range from 0% to 2%.

Preferably, the metal is one or more metals selected from copper, iron, gallium, silver, nickel, cobalt, palladium or platinum.

Preferably, the metal is located at the ion-exchange sites, in the pores and channels, on the surface and/or in the framework of the acidic microporous silicoaluminophosphate molecular sieve.

Preferably, the metal is introduced by one or more methods selected from situ synthesis, impregnation or ion exchange.

Preferably, the metals exist at ion-exchange sites as an ionic state, or exist in pores and channels or on the surface of the molecular sieve as a metallic oxide state, or are inset into the T atomic sites in the framework of the molecular sieve by isomorphous replacement.

Preferably, the catalyst contains a forming agent, and the mass fraction of the forming agent in the catalyst is in a range from 10% to 60%.

Preferably, the mass fraction of the forming agent in the catalyst is in a range from 10% to 30%.

Preferably, the forming agent is one or more compounds selected from alumina, silicon oxide or kaolin.

Preferably, the raw material acetal is expressed as $R_1O(CH_2O)_nR_2$, and n is selected from 1, 2, 3 or 4, and $R_1$ and $R_2$ are independently selected from $C_1$-$C_3$ alkyls. More preferably, the raw material acetal is preferably $CH_3OCH_2OCH_3$, $C_2H_5OCH_2OC_2H_5$ or $CH_3O(CH_2O)_2CH_3$.

The product acetal carbonyl compound with the structural unit of —O—(CO)—$CH_2$—O— or —O—$CH_2$—(CO)—O—, is formed by inserting one or more carbanyl group —CO— into the structural unit of —O—$CH_2$—O— in the molecular chain of raw material acetal $R_1O(CH_2O)_nR_2$.

The carbonylation process of acetal can be expressed as the following chemical reaction equations:

(I)

I

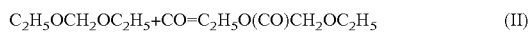

(II)

II

(III)

III

(IV)

IV

Preferably, the acetal carbonyl compound is one or more compounds selected from the following compounds: $CH_3$—O—(CO)—$CH_2$—O—$CH_3$, $C_2H_5$—O—(CO)—$CH_2$—O—$C_2H_5$, $CH_3$—O—(CO)—$CH_2$—O—$CH_2$—O—$CH_3$ or $CH_3$—O—$CH_2$—(CO)—O—$CH_2$—O—$CH_3$.

Preferably, the raw material carbon monoxide is obtained by separating from synthetic gas. In addition, in the method of the present invention, the feed gas can also be a mixed gas with volume content of carbon monoxide more than 50%, which may include hydrogen and one or more gases selected from or nitrogen, helium, argon, carbon dioxide, methane or ethane.

Preferably, the reaction conditions are as follows: the reaction temperature is in a range from 60° C. to 140° C., and the reaction pressure is in a range from 1 MPa to 15 MPa, and the mass space velocity of the raw material acetal is in a range from 0.1 $h^{-1}$ to 10.0 $h^{-1}$, and the molar ratio of the raw gas carbon monoxide to the raw material acetal is in a range from 2:1 to 20:1, and no solvent is added.

Preferably, the carbonylation reaction conditions are as follows: the reaction temperature is in a range from 70° C. to 120° C., and the reaction pressure is in a range from 3 MPa to 10 MPa, and the mass space velocity of the raw material acetal is in a range from 0.5 $h^{-1}$ to 3 $h^{-1}$, and the molar ratio of the raw material carbon monoxide to the raw material acetal is in a range from 5:1 to 15:1, and no solvent is added.

In the reaction, at least one of the raw acetal or the product acetal carbonyl compound is in liquid phase, and the acidic microporous silicoaluminophosphate molecular sieve is in solid phase, and the feed gas carbon monoxide is in gas phase, and therefore the reaction process is a gas-liquid-solid three phases reaction.

Preferably, the product acetal carbonyl compound can be further hydrogenated to prepare ethylene glycol ether. More preferably, the ethylene glycol ether is ethylene glycol monomethyl ether; and the ethylene glycol monomethyl ether can be hydrolyzed to prepare ethylene glycol.

Preferably, the reactor is a continuous reactor which is selected from a fixed bed reactor, a tank reactor, a moving bed reactor or a fluidized bed reactor.

Preferably, the reactor is one fixed bed reactor or more fixed bed reactors, to carry out a continuous reaction. The fixed bed reactor can be one or multiple. When multiple fixed bed reactors are used, the reactors can be connected in series, in parallel, or in combination of series and parallel.

EXAMPLES

The analysis method and the calculation method of conversion rate and selectivity in the Examples are as follows:

The constituent of the gas/liquid phase components were automatically analyzed by an Agilent7890 gas chromatograph equipped with an automatic sampler, an FID detector and FFAP capillary columns.

In some Examples of the present invention, the conversion of acetal and the selectivity of acetal carbonyl compound were calculated on the basis of the carbon molar number of the acetal:

Percent conversion of acetal=[(carbon molar number of acetal in the feeding material)−(carbon molar number of acetal in the discharging material)]÷(carbon molar number of acetal in the feeding material)×(100%)

Selectivity of acetal carbonyl compound=(carbon molar number of acetal carbonyl compound in the discharging material subtract the carbonyl groups)÷[(carbon molar number of acetal in the feeding material)−(carbon molar number of acetal in the discharging material)]×(100%)

The present invention is described in details by the following Examples, but the invention is not limited to these Examples.

Examples of Preparing the Catalyst

Example 1

Figure 2:
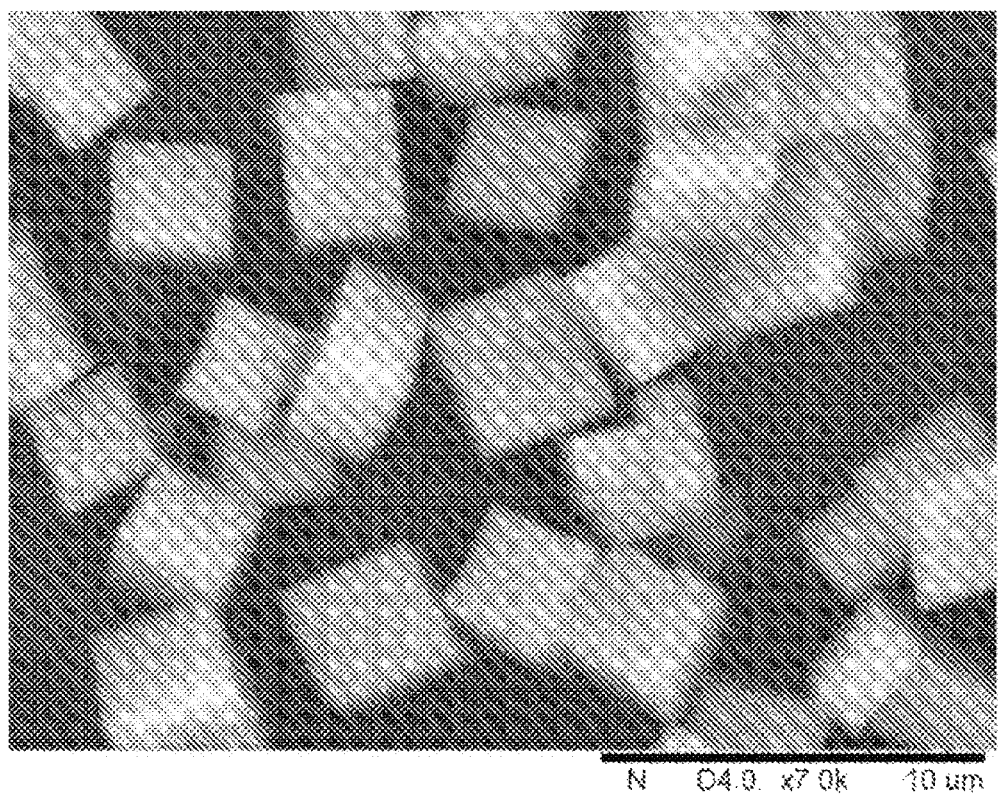
FIG. 2 is the scanning electron microscope (SEM) image of the SAPO-34 molecular sieve prepared in Example 1 of the present invention.

At room temperature, pseudo-boehmite was added into a phosphoric acid solution, stirring for 2h to obtain a homogeneous gel. Then silica sol and diethylamine (DEA) was added into the homogeneous gel, stirring for 3h to obtain a gel mixture with a molar ratio of 2.0 DEA:0.6 $SiO_2$:1.0 $Al_2O_3$:0.8 $P_2O_5$:50 $H_2O$. The gel mixture was put into a crystallization kettle with a polytetrafluoroethylene lining, and then crystallized for 2 days at 200° C. After finishing the crystallization and being cooled, the solid product was centrifugal separated, dried at 120° C., and then was put into a muffle furnace and calcined at 550° C. in air for 4 h to obtain a SAPO-34 molecular sieve raw powder sample with chemical composition of $(Si_{0.16}Al_{0.48}P_{0.36})O_2$. The SAPO-34 molecular sieve raw powder sample was calcined at 500° C. in air for 4 h to obtain an acidic SAPO-34 molecular sieve. The X-ray powder diffraction spectra and the scanning electron microscope image of the acidic SAPO-34 molecular sieve were shown in FIG. 1 and FIG. 2. And then the acidic SAPO-34 molecular sieve was molded using alumina as a forming agent, and the mass fraction of the forming agent in the catalyst is 20%, to obtain a cylindrical catalyst A with a diameter of 3 mm and a length of 3 mm.

Example 2

Aluminium isopropoxide, deionized water, phosphoric acid and tetraethoxysilane (TEOS) were mixed and stirred for 3h at room temperature to obtain a homogeneous gel. Then cetyl trimethyl ammonium bromide (CTAB) and diethylamine (DEA) solution were added into the homogeneous gel to obtain a gel mixture with a molar ratio of 2.0 DEA:1.0 $Al_2O_3$:0.8$P_2O_5$:0.4 TEOS:0.2 CTAB:100 $H_2O$. The gel mixture was put into a crystallization kettle with a polytetrafluoroethylene lining, and then crystallized for 1 day at 200° C. After finishing the crystallization and being cooled, the solid product was centrifugal separated, dried at 120° C., and then was put into a muffle furnace and calcined at 550° C. in air for 4 h to obtain a DNL-6 molecular sieve raw powder sample with chemical composition of $(Si_{0.14}Al_{0.37}P_{0.49})O_2$. The DNL-6 molecular sieve raw powder sample was calcined at 500° C. in air for 4 h to obtain an acidic DNL-6 molecular sieve. The acidic DNL-6 molecular sieve was molded using silicon oxide as a forming agent, and the mass fraction of the forming agent in the catalyst is 10%, to obtain a cylindrical catalyst B with a diameter of 3 mm and a length of 3 mm.

Example 3

At room temperature, pseudo-boehmite was added into a phosphoric acid solution, stirring for 2h to obtain a homogeneous gel. Then silica sol and diethylamine (DEA) was added into the homogeneous gel, stirring for 3h to obtain a gel mixture with a molar ratio of 2.0 DEA:0.6 $SiO_2$:1.0 $Al_2O_3$:0.8 $P_2O_5$:50 $H_2O$. The gel mixture was put into a crystallization kettle with a polytetrafluoroethylene lining, and then crystallized for 2 days at 200° C. After finishing the crystallization and being cooled, the solid product was centrifugal separated, dried at 120° C., and then was put into a muffle furnace and calcined at 550° C. in air for 4 h to obtain a SAPO-34 molecular sieve raw powder sample with chemical composition of $(Si_{0.16}Al_{0.4}P_{0.36})O_2$. The SAPO-34 molecular sieve raw powder sample was ion-exchanged with 0.8 mol/L aqueous solution of ammonium nitrate at 80° C. for 3 times, to obtain an ammonium type SAPO-34 molecular sieve. The ammonium type SAPO-34 molecular sieve was ion-exchanged with 0.05 mol/L aqueous solution of copper nitrate to obtain a SAPO-34 molecular sieve modified by copper using ion-exchange method. The SAPO-34 molecular sieve modified by copper using ion-exchange method was calcined at 500° C. in air for 4 h to obtain an acidic SAPO-34 molecular sieve with a copper mass fraction of 0.5%. And then the acidic SAPO-34 molecular sieve with a copper mass fraction of 0.5% was molded using alumina as a forming agent, and the mass fraction of the forming agent in the catalyst is 20%, to obtain a cylindrical catalyst C with a diameter of 3 mm and a length of 3 mm.

Example 4

Aluminium isopropoxide, deionized water, phosphoric acid and tetraethoxysilane (TEOS) were mixed and stirred for 3h at room temperature to obtain a homogeneous gel. Then cetyl trimethyl ammonium bromide (CTAB) and diethylamine (DEA) solution were added into the homogeneous gel to obtain a gel mixture with a molar ratio of 2.0 DEA:1.0 $Al_2O_3$:0.8$P_2O_5$:0.4 TEOS:0.2 CTAB:100 $H_2O$. The gel mixture was put into a crystallization kettle with a polytetrafluoroethylene lining, and then crystallized for 1 day at 200° C. After finishing the crystallization and being cooled, the solid product was centrifugal separated, dried at 120° C., and then was put into a muffle furnace and calcined at 550° C. in air for 4 h to obtain a DNL-6 molecular sieve raw powder sample with chemical composition of $(Si_{0.14}Al_{0.37}P_{0.49})O_2$. The DNL-6 molecular sieve raw powder sample was equivalent-volume impregnated with a palladium nitrate aqueous solution to obtain a DNL-6 molecular sieve modified by palladium using equivalent-volume impregnation method. The DNL-6 molecular sieve modified by palladium using equivalent-volume impregnation method was calcined at 500° C. in air for 4 h to obtain an acidic DNL-6 molecular sieve with a palladium mass fraction of 1%. The acidic DNL-6 molecular sieve was molded using silicon oxide as a forming agent, and the mass fraction of the forming agent in the catalyst is 10%, to obtain a cylindrical catalyst D with a diameter of 3 mm and a length of 3 mm.

Example 5

Pseudo-boehmite, silica sol, deionized water, phosphoric acid aqueous solution and hexamethyleneimine (HMI) were added to a beaker in sequence and mixed by stirring at room temperature to obtain a gel mixture with a molar ratio of 0.96 $P_2O_5$:1.0 $Al_2O_3$:1.0 $SiO_2$:1.51 HMT:55.47 $H_2O$. The gel mixture was put into a crystallization kettle with a polytetrafluoroethylene lining, and then crystallized for 1 day at 200° C. After finishing the crystallization and being cooled, the solid product was centrifugal separated, dried at 120° C., and then was put into a muffle furnace and calcined at 550° C. in air for 4 h to obtain a SAPO-35 molecular sieve raw powder sample with chemical composition of $(Si_{0.18}Al_{0.46}P_{0.36})O_2$. The SAPO-35 molecular sieve raw powder sample was equivalent-volume impregnated with a silver nitrate aqueous solution to obtain a SAPO-35 molecular sieve modified by silver using equivalent-volume impregnation method. The SAPO-35 molecular sieve modified by silver using equivalent-volume impregnation method was calcined at 500° C. in air for 4 h to obtain an acidic SAPO-35 molecular sieve with a silver mass fraction of 0.1%. The acidic SAPO-35 molecular sieve was molded using kaolin as a forming agent, and the mass fraction of the forming agent in the catalyst is 15%, to obtain a cylindrical catalyst E with a diameter of 3 mm and a length of 3 mm.

Example 6

Aluminium isopropoxide, silica sol, deionized water, phosphoric acid aqueous solution and cyclohexylamine (Cha) were added to a beaker in sequence and mixed by stirring at room temperature to obtain a gel mixture with a molar ratio of 0.11 $SiO_2$:1 $Al_2O_3$:1 $P_2O_5$:1 Cha:50$H_2O$. The gel mixture was put into a crystallization kettle with a polytetrafluoroethylene lining, and then crystallized for 1 day at 200° C. After finishing the crystallization and being cooled, the solid product was centrifugal separated, dried at 120° C., and then was put into a muffle furnace and calcined at 550° C. in air for 4 h to obtain a SAPO-17 molecular sieve raw powder sample with chemical composition of $(Si_{0.14}Al_{0.51}P_{0.35})_2$. The SAPO-17 molecular sieve raw powder sample was equivalent-volume impregnated with a nickel nitrate aqueous solution to obtain a SAPO-17 molecular sieve modified by nickel using equivalent-volume impregnation method. The SAPO-17 molecular sieve modified by nickel using equivalent-volume impregnation method was calcined at 500° C. in air for 4 h to obtain an acidic SAPO-17 molecular sieve with a nickel mass fraction of 2%. The acidic SAPO-17 molecular sieve was molded using alumina as a forming agent, and the mass fraction of the forming agent in the catalyst is 30%, to obtain a cylindrical catalyst F with a diameter of 3 mm and a length of 3 mm.

Example 7

Pseudo-boehmite, silica sol, deionized water, phosphoric acid aqueous solution and N,N-diisopropylethylamine ($C_8H_{19}N$) were added to a beaker in sequence and mixed by stirring at room temperature to obtain a gel mixture with a molar ratio of 0.2 $SiO_2$:1.0 $Al_2O_3$:1.0 $P_2O_5$:1.6 $C_8H_{19}N$: 55$H_2O$. The gel mixture was put into a crystallization kettle with a polytetrafluoroethylene lining, and then crystallized for 3 days at 180° C. After finishing the crystallization and being cooled, the solid product was centrifugal separated, dried at 120° C., and then was put into a muffle furnace and calcined at 550° C. in air for 4 h to obtain a SAPO-18 molecular sieve raw powder sample with 0.7 chemical composition of $(Si_{0.11}Al_{0.57}P_{0.32})O_2$. The SAPO-18 molecular sieve raw powder sample was equivalent-volume impregnated with a gallium nitrate aqueous solution to obtain a SAPO-18 molecular sieve modified by gallium using equivalent-volume impregnation method. The SAPO-18 molecular sieve modified by gallium using equivalent-volume impregnation method was calcined at 500° C. in air for 4 h to obtain an acidic SAPO-18 molecular sieve with a gallium mass fraction of 0.3%. The acidic SAPO-18 molecular sieve was molded using alumina as a forming agent, and the mass fraction of the forming agent in the catalyst is 20%, to obtain a cylindrical catalyst G with a diameter of 3 mm and a length of 3 mm.

Example 8

Pseudo-boehmite, silica sol, deionized water, phosphoric acid aqueous solution and N,N,N',N'-tetramethyl-1,6-hexamethylenediamine (TMHD) were added to a beaker in sequence and mixed by stirring at room temperature to obtain a gel mixture with a molar ratio of 2.0 TMHD:0.6 $SiO_2$:0.8 $Al_2O_3$:$P_2O_5$:40 $H_2O$. The gel mixture was put into a crystallization kettle with a polytetrafluoroethylene lining, and then crystallized for 3 days at 200° C. After finishing the crystallization and being cooled, the solid product was centrifugal separated, dried at 120° C., and then was put into a muffle furnace and calcined at 550° C. in air for 4 h to obtain a SAPO-56 molecular sieve raw powder sample with chemical composition of $(Si_{0.10}Al_{0.42}P_{0.48})O_2$. The SAPO-56 molecular sieve raw powder sample was ion-exchanged with 0.8 mol/L aqueous solution of ammonium nitrate at 80° C. for 3 times, to obtain an ammonium type SAPO-56 molecular sieve. The ammonium type SAPO-56 molecular sieve was ion-exchanged with 0.04 mol/L aqueous solution of copper nitrate to obtain a SAPO-56 molecular sieve modified by copper using ion-exchange method. The SAPO-56 molecular sieve modified by copper using ion-exchange method was calcined at 500° C. in air for 4 h to obtain an acidic SAPO-56 molecular sieve with a copper mass fraction of 0.3%. And then the acidic SAPO-56 molecular sieve with a copper mass fraction of 0.3% was molded using alumina as a forming agent, and the mass fraction of the forming agent in the catalyst is 20%, to obtain a cylindrical catalyst H with a diameter of 3 mm and a length of 3 mm.

Comparative Example 1

Y molecular sieve with Si/Al=2.3 was employed, which was purchased from the catalyst plant of Nankai University. The Y molecular sieve was ion-exchanged with 0.8 mol/L aqueous solution of ammonium nitrate at 80° C. for 3 times, to obtain an ammonium type Y molecular sieve. The ammonium type Y molecular sieve was ion-exchanged with 0.05 mol/L aqueous solution of copper nitrate to obtain a Y molecular sieve modified by copper using ion-exchange method. The Y molecular sieve modified by copper using ion-exchange method was calcined at 500° C. in air for 4 h to obtain an acidic Y molecular sieve with a copper mass fraction of 0.5%. And then the acidic Y molecular sieve with a copper mass fraction of 0.5% was molded using alumina as a forming agent, and the mass fraction of the forming agent in the catalyst is 20%, to obtain a cylindrical catalyst I with a diameter of 3 mm and a length of 3 mm.

Examples of Testing Catalyst Performance

Example 9

1.0 kg of Catalyst A was loaded into a stainless steel fixed bed reactor with an inner diameter of 32 mm, activated at 500° C. for 4 hours under nitrogen gas at atmospheric pressure. The temperature was reduced to the reaction temperature (abbreviated as T) of 90° C., and then a fresh feed gas with a molar ratio of 7 CO:1 $CH_3OCH_2OCH_3$ was introduced, and the pressure was increased to the reaction pressure (abbreviated as P) of 15 MPa, and the weight hourly space velocity (abbreviated as WHSV) of $CH_3OCH_2OCH_3$ in the fresh feed gas was controlled as 0.1 $h^{-1}$. After the reaction was stable, the reaction products were analyzed by the gas chromatograph and the percent conversion of acetal and the single pass selectivity of acetal carbonyl compound were calculated. The results were shown in Table 1.

Example 10

1.0 kg of Catalyst B was loaded into a stainless steel fixed bed reactor with an inner diameter of 32 mm, activated at 500° C. for 4 hours under nitrogen gas at atmospheric pressure. The temperature was reduced to the reaction temperature (abbreviated as T) of 60° C., and then a fresh feed gas with a molar ratio of 13 CO:1 $CH_3OCH_2OCH_3$ was introduced, and the pressure was increased to the reaction pressure (abbreviated as P) of 1 MPa, and the weight hourly space velocity (abbreviated as WHSV) of $CH_3OCH_2OCH_3$ in the fresh feed gas was controlled as 10 $h^{-1}$. After the reaction was stable, the reaction products were analyzed by the gas chromatograph and the percent conversion of acetal and the single pass selectivity of acetal carbonyl compound were calculated. The results were shown in Table 1.

Example 11

1.0 kg of Catalyst C was loaded into a stainless steel fixed bed reactor with an inner diameter of 32 mm, activated at 500° C. for 4 hours under nitrogen gas at atmospheric pressure. The temperature was reduced to the reaction temperature (abbreviated as T) of 90° C., and then a fresh feed gas with a molar ratio of 7 CO:1 $CH_3OCH_2OCH_3$ was introduced, and the pressure was increased to the reaction pressure (abbreviated as P) of 15 MPa, and the weight hourly space velocity (abbreviated as WHSV) of $CH_3OCH_2OCH_3$ in the fresh feed gas was controlled as 0.1 $h^{-1}$. After the reaction was stable, the reaction products were analyzed by the gas chromatograph and the percent conversion of acetal and the single pass selectivity of acetal carbonyl compound were calculated. The results were shown in Table 1.

Example 12

1.0 kg of Catalyst D was loaded into a stainless steel fixed bed reactor with an inner diameter of 32 mm, activated at 500° C. for 4 hours under nitrogen gas at atmospheric pressure. The temperature was reduced to the reaction temperature (abbreviated as T) of 60° C., and then a fresh feed gas with a molar ratio of 13 CO:1 $CH_3OCH_2OCH_3$ was introduced, and the pressure was increased to the reaction pressure (abbreviated as P) of 1 MPa, and the weight hourly space velocity (abbreviated as WHSV) of $CH_3OCH_2OCH_3$ in the fresh feed gas was controlled as 10 $h^{-1}$. After the reaction was stable, the reaction products were analyzed by the gas chromatograph and the percent conversion of acetal and the single pass selectivity of acetal carbonyl compound were calculated. The results were shown in Table 1.

Example 13

1.0 kg of Catalyst E was loaded into a stainless steel fixed bed reactor with an inner diameter of 32 mm, activated at 500° C. for 4 hours under nitrogen gas at atmospheric pressure. The temperature was reduced to the reaction temperature (abbreviated as T) of 140° C., and then a fresh feed gas with a molar ratio of 2 CO:1 $CH_3OCH_2OCH_3$ was introduced, and the pressure was increased to the reaction pressure (abbreviated as P) of 6.5 MPa, and the weight hourly space velocity (abbreviated as WHSV) of $CH_3OCH_2OCH_3$ in the fresh feed gas was controlled as 3.0 $h^{-1}$. After the reaction was stable, the reaction products were analyzed by the gas chromatograph and the percent conversion of acetal and the single pass selectivity of acetal carbonyl compound were calculated. The results were shown in Table 1.

Example 14

1.0 kg of Catalyst F was loaded into a stainless steel fixed bed reactor with an inner diameter of 32 mm, activated at 500° C. for 4 hours under nitrogen gas at atmospheric pressure. The temperature was reduced to the reaction temperature (abbreviated as T) of 140° C., and then a fresh feed gas with a molar ratio of 2 CO:1 $CH_3OCH_2OCH_3$ was introduced, and the pressure was increased to the reaction pressure (abbreviated as P) of 6.5 MPa, and the weight hourly space velocity (abbreviated as WHSV) of $CH_3OCH_2OCH_3$ in the fresh feed gas was controlled as 3.0 $h^{-1}$. After the reaction was stable, the reaction products were analyzed by the gas chromatograph and the percent conversion of acetal and the single pass selectivity of acetal carbonyl compound were calculated. The results were shown in Table 1.

Example 15

1.0 kg of Catalyst G was loaded into a stainless steel fixed bed reactor with an inner diameter of 32 mm, activated at 500° C. for 4 hours under nitrogen gas at atmospheric pressure. The temperature was reduced to the reaction temperature (abbreviated as T) of 73° C., and then a fresh feed gas with a molar ratio of 10 CO:1 $CH_3OCH_2OCH_3$ was introduced, and the pressure was increased to the reaction pressure (abbreviated as P) of 2.0 MPa, and the weight hourly space velocity (abbreviated as WHSV) of $CH_3OCH_2OCH_3$ in the fresh feed gas was controlled as 0.3 $h^{-1}$. After the reaction was stable, the reaction products were analyzed by the gas chromatograph and the percent conversion of acetal and the single pass selectivity of acetal carbonyl compound were calculated. The results were shown in Table 1.

Example 16

1.0 kg of Catalyst H was loaded into a stainless steel fixed bed reactor with an inner diameter of 32 mm, activated at 500° C. for 4 hours under nitrogen gas at atmospheric pressure. The temperature was reduced to the reaction temperature (abbreviated as T) of 120° C., and then a fresh feed gas with a molar ratio of 15 CO:1 $CH_3OCH_2OCH_3$ was introduced, and the pressure was increased to the reaction pressure (abbreviated as P) of 4.7 MPa, and the weight hourly space velocity (abbreviated as WHSV) of $CH_3OCH_2OCH_3$ in the fresh feed gas was controlled as 0.5 $h^{-1}$. After the reaction was stable, the reaction products were analyzed by the gas chromatograph and the percent conversion of acetal and the single pass selectivity of acetal carbonyl compound were calculated. The results were shown in Table 1.

Comparative Example 2

The experimental conditions were same as Example 11, except that the Catalyst C was changed to the Catalyst I. The results were shown in Table 1.

TABLE 1

Results of the carbonylation reaction of acetal

| | Catalyst | Percent conversion of the acetal (%) | Selectivity of the acetal carbonyl compound (%) | Single pass life of the catalyst (days) |
| --- | --- | --- | --- | --- |
| Example 9 | A | 100 | 93.2 | 430 |
| Example 10 | B | 100 | 92.3 | 410 |
| Example 11 | C | 100 | 95.8 | 450 |
| Example 12 | D | 100 | 94.1 | 430 |
| Example 13 | E | 100 | 95.6 | 500 |
| Example 14 | F | 100 | 96.3 | 510 |
| Example 15 | G | 100 | 97.8 | 550 |
| Example 16 | H | 100 | 96.1 | 530 |
| Comparative Example 2 | I | 38 | 72.5 | 19 |

The present invention has been described in detail as above, but the invention is not limited to the detailed embodiments described in this text. Those skilled in the art will understand that other changes and deformations can be made without deviating from the scope of the invention. The scope of the invention is limited by the appended claims.

The invention claimed is:

1. A method for preparing acetal carbonyl compound used as an intermediate for producing ethylene glycol, which comprises a step in which a raw material acetal and carbon monoxide go through a reactor loaded with a catalyst for carrying out a carbonylation reaction; wherein the catalyst contains an acidic microporous silicoaluminophosphate molecular sieve; wherein the chemical composition of the acidic microporous silicoaluminophosphate molecular sieve is expressed as $(Si_xAl_yP_z)O_2$, and x is in a range from 0.01 to 0.60, and y is in a range from 0.2 to 0.60, and z is in a range from 0.2 to 0.60, and x+y+z=1; wherein the raw material acetal is expressed as $R_1O(CH_2O)_nR_2$, and n is selected from 1, 2, 3 or 4, and $R_1$ and $R_2$ are independently selected from $C_1$-$C_3$ alkyls; wherein the acidic microporous silicoaluminophosphate molecular sieve is one or more molecular sieves selected from the molecular sieves with framework type of CHA, RHO, LEV, ERI, AEI or AFX.

2. A method for preparing acetal carbonyl compound used as an intermediate for producing ethylene glycol according to claim 1, wherein the acidic microporous silicoaluminophosphate molecular sieve ahas an 8-membered ring pore framework.

3. A method for preparing acetal carbonyl compound used as an intermediate for producing ethylene glycol according to claim 1, wherein the acidic microporous silicoaluminophosphate molecular sieve is one or more molecular sieves selected from SAPO-34, DNL-6, SAPO-35, SAPO-17, SAPO-18 or SAPO-56.

4. A method for preparing acetal carbonyl compound used as an intermediate for producing ethylene glycol according to claim 1, wherein the acidic microporous silicoaluminophosphate molecular sieve contains a metal; and the mass fraction of the metal element in the acidic microporous silicoaluminophosphate molecular sieve is in a range from 0% to 10%.

5. A method for preparing acetal carbonyl compound used as an intermediate for producing ethylene glycol according to claim 4, wherein the metal is located at the ion-exchange sites, in the pores and channels, on the surface and/or in the framework of the acidic microporous silicoaluminophosphate molecular sieve; and the metal is introduced by one or more methods selected from in-situ synthesis, impregnation or ion exchange.

6. A method for preparing acetal carbonyl compound used as an intermediate for producing ethylene glycol according to claim 1, wherein the catalyst contains a forming agent, and the mass fraction of the forming agent in the catalyst is in a range from 10% to 60%.

7. A method for preparing acetal carbonyl compound used as an intermediate for producing ethylene glycol according to claim 1, wherein the raw material acetal is $CH_3OCH_2OCH_3$, $C_2H_5OCH_2OC_2H_5$ or $CH_3O(CH_2O)_2CH_3$, and the acetal carbonyl compound is one or more compounds selected from $CH_3$—O—(CO)—$CH_2$—O—$CH_3$, $C_2H_5$—O—(CO)—$CH_2$—O—$C_2H_5$, $CH_3$—O—(CO)—$CH_2$—O—$CH_2$—O—$CH_3$ or $CH_3$—O—$CH_2$—(CO)—O—$CH_2$—O—$CH_3$.

8. A method for preparing acetal carbonyl compound used as n intermediate for producing ethylene glycol according to claim 1, wherein the carbonylation reaction conditions are as follows: the reaction temperature is in a range from 60° C. to 140° C., and the reaction pressure is in a range from 1 MPa to 15 MPa, and the mass space velocity of the raw material acetal is in a range from 0.1 $h^{-1}$ to 10.0 $h^{-1}$, and the molar ratio of carbon monoxide to the raw material acetal is in a range from 2:1 to 20:1, and no solvent is added.

9. A method for preparing acetal carbonyl compound used as an intermediate for producing ethylene glycol according to claim 1, wherein the reactor is a continuous reactor which is selected from a fixed bed reactor, a tank reactor, a moving bed reactor or a fluidized bed reactor.

10. A method for preparing acetal carbonyl compound used as an intermediate for producing ethylene glycol according to claim 4, wherein the mass fraction of the metal element in the acidic microporous silicoaluminophosphate molecular sieve is in a range from 0% to 2%.

11. A method for preparing acetal carbonyl compound used as an intermediate for producing ethylene glycol according to claim 4, wherein the metal is one or more metals selected from copper, iron, gallium, silver, nickel, cobalt, palladium or platinum.

12. A method for preparing acetal carbonyl compound used as an intermediate for producing ethylene glycol according to claim 6, wherein the mass fraction of the forming agent in the catalyst is in a range from 10% to 30%.

13. A method for preparing acetal carbonyl compound used as an intermediate for producing ethylene glycol according to claim 6, wherein the forming agent is one or more compounds selected from alumina, silicon oxide or kaolin.

14. A method for preparing acetal carbonyl compound used as an intermediate for producing ethylene glycol according to claim 1, wherein the carbonylation reaction conditions are as follows: the reaction temperature is in a range from 70° C. to 120° C., and the reaction pressure is in a range from 3 MPa to 10 MPa, and the mass space velocity of the raw material acetal is in a range from 0.5 $h^{-1}$ to 3 $h^{-1}$, and the molar ratio of carbon monoxide to the raw material acetal is in a range from 5:1 to 15:1, and no solvent is added.

* * * * *